(12) United States Patent
Bitler

(10) Patent No.: US 7,101,928 B1
(45) Date of Patent: Sep. 5, 2006

(54) POLYMERIC THICKENERS FOR OIL-CONTAINING COMPOSITIONS

(75) Inventor: Steven P. Bitler, Menlo Park, CA (US)

(73) Assignee: Landec Corporation, Menlo Park, CA (US)

( * ) Notice: Subject to any disclaimer, the term of this patent is extended or adjusted under 35 U.S.C. 154(b) by 0 days.

(21) Appl. No.: 09/398,377

(22) Filed: Sep. 17, 1999

(51) Int. Cl.
*C08K 5/01* (2006.01)
*C08K 5/10* (2006.01)
*A61K 47/30* (2006.01)

(52) U.S. Cl. .............. 524/474; 524/265; 524/310; 524/313; 524/314; 524/315; 524/318; 524/801; 524/484; 524/485; 524/486; 514/772.1; 514/772.3; 514/772.4; 514/772.5; 514/772.7; 514/844; 514/938

(58) Field of Classification Search .............. 524/265, 524/310, 313, 314, 315, 318, 474, 801, 484, 524/485, 486; 514/772.1, 772.3, 772.4, 772.5, 514/772.7, 844, 938, 939
See application file for complete search history.

(56) References Cited

U.S. PATENT DOCUMENTS

| | | | | |
|---|---|---|---|---|
| 3,355,394 A | * | 11/1967 | Korbanka et al. | 524/313 |
| 3,772,196 A | * | 11/1973 | St. Claire et al. | 508/264 |
| 3,892,671 A | * | 7/1975 | Song et al. | 508/264 |
| 3,894,958 A | * | 7/1975 | McCoy et al. | 508/470 |
| 3,915,843 A | * | 10/1975 | Franck et al. | 208/112 |
| 4,057,622 A | * | 11/1977 | Hase et al. | 514/939 |
| 4,057,623 A | * | 11/1977 | Hase et al. | 514/939 |
| 4,057,624 A | * | 11/1977 | Hase et al. | 514/939 |
| 4,261,845 A | | 4/1981 | Cuscurida | 252/51.5 |
| 4,720,303 A | | 1/1988 | Soldatos | |
| 4,737,541 A | | 4/1988 | Stavenger et al. | 524/547 |
| 4,794,139 A | | 12/1988 | Braden et al. | 524/117 |
| 4,839,166 A | | 6/1989 | Grollier et al. | 424/71 |
| 4,877,557 A | * | 10/1989 | Kaneshige et al. | 508/306 |
| 4,927,627 A | | 5/1990 | Schrader et al. | 424/62 |
| 4,939,179 A | | 7/1990 | Cheney et al. | 514/789 |
| 4,971,722 A | | 11/1990 | Phillippsen | 252/315.1 |
| 4,976,961 A | * | 12/1990 | Norbury et al. | 424/401 |
| 5,021,525 A | | 6/1991 | Montague et al. | 526/210 |
| 5,086,142 A | | 2/1992 | Fock et al. | 526/318 |
| 5,112,601 A | | 5/1992 | Sebag et al. | 424/61 |
| 5,217,636 A | * | 6/1993 | Paboucek | 508/473 |
| 5,247,121 A | | 9/1993 | Sebag et al. | 560/24 |
| 5,256,737 A | | 10/1993 | Barzaghi | 525/328.9 |
| 5,270,379 A | | 12/1993 | McAndrew et al. | 524/555 |
| 5,281,329 A | * | 1/1994 | Mueller et al. | 208/370 |
| 5,318,995 A | | 6/1994 | Mondet et al. | 514/772.1 |
| 5,319,055 A | | 6/1994 | Sperry et al. | 528/49 |
| 5,415,790 A | | 5/1995 | Maeda et al. | 252/8.6 |
| 5,422,233 A | | 6/1995 | Eckert et al. | 430/466 |
| 5,442,054 A | | 8/1995 | Kieserwetter et al. | 536/84 |
| 5,516,544 A | | 5/1996 | Sekula et al. | 426/611 |
| 5,519,063 A | * | 5/1996 | Mondet et al. | 514/772.4 |
| 5,525,128 A | | 6/1996 | McAleer et al. | 44/459 |
| 5,530,045 A | | 6/1996 | Brena et al. | 524/376 |
| 5,610,002 A | | 3/1997 | Ross et al. | 430/54.6 |
| 5,736,125 A | | 4/1998 | Morawsky et al. | 44/59 |
| 6,238,447 B1 | | 5/2001 | More | 44/393 |
| 6,475,495 B1 | | 11/2002 | Maignan et al. | 424/401 |
| 2003/0186824 A1 | * | 10/2003 | Chiu et al. | 508/490 |

FOREIGN PATENT DOCUMENTS

| | | | |
|---|---|---|---|
| EP | 0803513 | 10/1997 | |
| FR | 2131111 | 11/1972 | |
| JP | 59-185813 | * 10/1984 | |
| JP | 100534 | * 4/1992 | 524/265 |
| JP | 07-220531 | * 8/1995 | |
| WO | WO 96/27641 | 9/1996 | |
| WO | WO 98/25710 | 6/1998 | |

* cited by examiner

Primary Examiner—Peter Szekely
(74) Attorney, Agent, or Firm—Sheldon & Mak; Jeffrey G. Sheldon

(57) ABSTRACT

Novel thickeners for oil-containing compositions are crystalline polymers, preferably side chain crystalline polymers, which (a) have a crystalline melting point, $T_p$, and an onset of melting temperature, $T_o$, such that $T_p-T_o$ is less than $T_p^{0.7}$; (b) are soluble in the oil at temperatures above $T_p$, and (c) have been dispersed in the oil by a process which comprises (i) dissolving the polymer in the oil at a temperature above $T_p$, and (ii) cooling the solution from step (i) to crystallize the polymer in the oil.

53 Claims, No Drawings

POLYMERIC THICKENERS FOR OIL-CONTAINING COMPOSITIONS

BACKGROUND OF THE INVENTION

1. Field of the Invention

This invention relates to polymeric thickeners for oil-containing compositions.

2. Introduction to the Invention

It is known to use polymers containing functional groups to thicken oil-containing compositions. Reference may be made for example to U.S. Pat. Nos. 3,355,394, 4,057,622, 4,057,623, 4,057,624, 4,720,303, 4,737,541, 4,794,139, 4,839,166, 4,939,179, 4,971,722, 5,053,057, 5,086,142, 5,112,601, 5,192,462, 5,247,121, 5,256,737, 5,270,379, 5,318,995, 5,319,055, 5,415,790, 5,422,233, 5,442,054, 5,516,544, 5,519,063, 5,530,045, 5,610,002 and 5,736125. The entire disclosure of each of those United States patents is incorporated herein by reference for all purposes.

SUMMARY OF THE INVENTION

I have discovered, in accordance with the present invention, that oil-containing compositions can be thickened with crystalline polymers which contain long chain alkyl groups in side chains but which are substantially free of functional groups. The thickened oil compositions of the invention comprise (1) an oil, and
(2) dispersed in the oil, a polymer which
  (a) has a crystalline melting point, $T_p$, and an onset of melting temperature, $T_o$, such that $T_p - T_o$ is less than $T_p^{0.7}$;
  (b) is soluble in the oil at temperatures above $T_p$,
  (c) has been dispersed in the oil by a process which comprises (i) dissolving the polymer in the oil at a temperature above $T_p$, and (ii) cooling the solution to crystallize the polymer in the oil, and
  (d) is a side chain crystalline (SCC) polymer which is substantially free of functional groups;

the composition being at a temperature below $T_p$.

The composition must be maintained at a temperature below $T_p$, since the polymer will cease to have a thickening effect if it redissolves in the oil. The composition can be free of water, or can be a water-in-oil emulsion.

One of the advantages which results from the use of such polymers as thickening agents is that they reduce or remove the need to use surface active agents in water-in-oil emulsions. This is particularly useful in personal care products, since it is conventional for such products to contain surfactants which can cause an adverse reaction when they contact human skin.

DETAILED DESCRIPTION OF THE INVENTION

Definitions and Abbreviations

In this specification, parts and percentages are by weight. Temperatures are in ° C. The onset of melting, $T_o$, the peak melting temperature, $T_p$, and the heat of fusion, J/g, are determined using a differential scanning calorimeter (DSC), at a rate of temperature change of 10° C./min, typically from −10 to 150° C., and on the second heat cycle. $T_o$ and $T_p$ are measured in the conventional way well known to those skilled in the art. Thus $T_p$ is the temperature at the peak of the DSC curve, and $T_o$ is the temperature at the intersection of the baseline of the DSC peak and the onset line, the onset line being defined as the tangent to the steepest part of the DSC curve below $T_p$. The abbreviations Mn and Mw are used to denote number average and weight average molecular weight in daltons, respectively, measured in tetrahydrofuran using size exclusion chromatography, configured with a Wyatt laser light scattering detector. Bulk viscosities given in the Example for the polymeric thickeners are in centipoise and were measured using a Brookfield LVT viscometer with an electrically thermostatted Thermosel heater, controlled for example to 95° C., and small sample adapter using spindles 4 and 7. The procedure used in the Example to compare the effectiveness of the polymeric thickeners was as follows. 5 parts of the thickener were dissolved in 95 parts of hydrogenated polyisobutylene (HPIB) with stirring at 120° C. (HPIB is a light oil). The resulting solution was placed in an incubator at 20° C. for 16 hours. The viscosity of cooled product in centipoise was determined using a Brookfield DV-|+ digital viscometer with CP-51 spindle using a sample adapter which was thermostatically controlled, for example, to 25° C. The viscosities were measured after four minutes at a speed of 2.5 rpm, i.e. after 10 revolutions. The abbreviation CxA is used to denote an n-alkyl acrylate in which the n-alkyl group contains x carbon atoms, the abbreviation Cx alkyl is used to denote an n-alkyl group which contains x carbon atoms, and the abbreviation CxM is used to denote an n-alkyl methacrylate in which the n-alkyl group contains x carbon atoms. Other abbreviations are given elsewhere in the specification.

The Polymeric Thickeners The SCC polymers used as thickeners in the present invention are crystalline, this term being used to include polymers containing a crystalline polymeric moiety which is chemically bound to a non-crystalline moiety. The thickener can be a single polymer or a mixture of polymers, and the polymer can be a homopolymer, or a copolymer of two or more comonomers, including random copolymers, graft copolymers, block copolymers and thermoplastic elastomers. The SCC polymer may for example be derived from one or more acrylic, methacrylic, olefinic, epoxy, vinyl, ester-containing, amide-containing or ether-containing monomers. The molecular weight of an SCC polymer is relatively unimportant to its $T_p$, but is generally an important factor in determining the $T_p$ of other polymers.

It is important that the SCC polymer should melt over a relatively small temperature range. The closer $T_p$ is to room temperature, the more rapid the transition should preferably be. Thus $T_p - T_o$ is less than $T_p^{0.7}$, particularly less than $T_p^{0.6}$, $T_o$ and $T_p$ being in ° C. Tp can vary widely, depending on the conditions under which the composition is to be used, as further discussed below. $T_p - T_o$ is preferably less than 10° C., particularly less than 6° C.

The SCC polymers used in the present invention are in themselves well known. Publications describing SCC polymers include U.S. Pat. Nos. 4,830,855, 5,120,349, 5,156,911, 5,387,450, 5,412,035, 5,665,822, 5,783,302, 5,752,925, 5,807,291, 5,469,867, and 5,826,584; J. Poly. Sci. 60, 19 (1962), J. Poly. Sci, (Polymer Chemistry) 7, 3053 (1969), 9, 1835, 3349, 3351, 3367, 10, 1657, 3347, 18, 2197, 19, 1871, J. Poly. Sci, Poly-Physics Ed 18 2197 (1980), J. Poly. Sci, Macromol. Rev, 8, 117 (1974), Macromolecules 12, 94 (1979), 13, 12, 15, 18, 2141, 19, 611, JACS 75, 3326 (1953), 76; 6280, Polymer J 17, 991 (1985); and Poly. Sci USSR 21, 241 (1979). The disclosure of each of those U.S. patents is incorporated herein by reference for all purposes.

The SCC polymer used in this invention can be a homopolymer, or a copolymer of two or more comonomers, including random copolymers, graft copolymers, block copolymers and thermoplastic elastomers. The number average molecular weight of the SCC polymer is generally from 10,000 to 1,500,000, preferably 12,000 to 1,000,000. In one preferred embodiment, the SCC polymer is substantially free of functional groups and consists essentially of units derived from least one n-alkyl acrylate or methacrylate in which the n-alkyl group contains 12 to 50, preferably 16 to 50, carbon atoms. In another preferred embodiment, the SCC polymer is substantially free of functional groups and consists essentially of units derived from (i) at least 50% of at least one n-alkyl acrylate or methacrylate in which the n-alkyl group contains 12 to 50, preferably 16 to 50, carbon atoms, and (ii) less than 50% of at least one alkyl acrylate or methacrylate in which the alkyl group is not an n-alkyl group containing 12 to 50 carbon atoms.

Preferred SCC polymers comprise side chains comprising linear polymethylene moieties containing 10 to 50, especially 14 to 22, carbon atoms, or linear perfluorinated or substantially perfluorinated polymethylene moieties containing 6 to 50 carbon atoms. Polymers containing such side chains can be prepared by polymerizing one or more corresponding linear aliphatic acrylates or methacrylates, or equivalent monomers such as acrylamides or methacrylamides. A number of such monomers are available commercially, either as individual monomers or as mixtures of identified monomers, for example C12A, C14A, C16A, C18A, C22A, a mixture of C18A, C20A and C22A, a mixture of C26A to C40A, fluorinated C8A (AE800 from American Hoechst) and a mixture of fluorinated C8A, C10A and C12A (AE12 from American Hoechst).

When the SCC polymer is a graft or block copolymer, it can be formed either by copolymerizing a vinyl type macromonomer with other monomers, or by making an SCC polymer, and then reacting the functionalized polymer with the second block material, for example a urethane or epoxy block, polyethyleneoxide or polypropyleneoxide or polytetramethyleneoxide and the like polyether blocks, polysiloxane or poly(alkyl or alkoxy)silane blocks.

The SCC polymer should contain sufficient long chain groups that it will dissolve in the oil at the temperature above $T_p$. When the SCC polymer is used to thicken and oil, or mixture of oils, which is free from water, it generally contains at least 50%, preferably at least 60%, particularly at least 80%, of units derived from a long chain monomer, and can contain up to 100% of such units.

The molecular weight of the thickening polymer should be sufficiently high that the polymer, after it has been dissolved in the oil, will precipitate from the oil when the heated mixture is cooled, for example to a temperature at least 10–20° C. below $T_p$, thus producing an opaque mixture. This is believed to result in the formation of a polymer network in which the polymer crystallites are connected to one another by semisoluble chains.

The $T_p$ of the thickening polymer is preferably 10–40° C. above, particularly 10–30° C. above, especially about 20° C. above, the temperature at which the composition is to be used. It appears that the oil plasticizes the thickening polymer, so that its melting point in the composition is for example 5–10° C. lower than $T_p$, and it is therefore important that $T_p$ is sufficiently above the temperature of use to ensure that the thickening polymer does not melt during use. Thus for compositions to be used at 20–25° C. the thickening polymer preferably has a $T_p$ of above 40° C., preferably 40–50° C. If the $T_p$ of the thickening polymer is too far above the temperature of use, this can result in excessive precipitation of the polymer and a reduction in the thickening effect. It is preferred, therefore, that $T_p$ is not more than 30° C., preferably not more than 20° C., above the temperature of use. Depending on the expected temperature of use, $T_p$ may be from 0–150° C. generally 10–100° C. for example 20–80° C.

The polymeric thickener should be used in an amount sufficient to thicken the composition to the desired thickness, in general 0.1 to 12% by weight based on the oil, for example 2–10% by weight based on the composition. The amount of the polymeric thickener preferably used varies with the application. It is usually unnecessary to use more than 10% of the total composition, e.g. 3–10%, and smaller amounts such as 3 to 7%, for example about 5%, are often effective.

Oils

The new polymeric thickeners are effective with a broad range of oils. Suitable oils are disclosed, for example, at column three, line 37, to column 4, line 4, of U.S. Pat. No. 5,736,125, and elsewhere in the documents incorporated by reference herein.

Compositions

The new polymeric thickeners are useful for thickening a wide variety of compositions. The compositions can be free from water, or can be water-in-oil emulsions. The invention is particularly useful for cosmetic (including hair care) compositions. Such compsitions can for example be in the form of varnishes, gels, sticks, oil-in-water creams, water-in-oil creams, and thickened oil products with or without water. Specific examples of such compositions include, but are not limited to lipstick, deodorant sticks, nail varnishes, pretanning lotions, sunscreen lotions, sun tan lotions, after-sun-lotions, sun creams, protective hand creams, night renewal creams, body milks and lotions, light facial cream, protective day creams, liquid moisturizing emulsions, hairdressing preparations (including hair-treating oils, shampoos, after-shampoo compositions, products for rinsing to be applied before or after shampooing, before or after dyeing or bleaching, before or after permanent-waving or hair straightening, as a hair-setting or blow-drying composition, as a restructuring composition, or as a support for permanent-waving or for dyeing or bleaching hair), foam baths, bath oils, skin cleansers, skin foundations mascaras, eye makeups, makeup removers designed to assist in removing other cosmetics compositions. The cosmetic compositions can contain conventional additives for cosmetic compositions, including but not limited to fragnances, sun screen agents, colorants, pigments, silicones, deodorants and antiseptic agents. However, the invention is also useful in othe contexts, for example in paints, film-forming compositions, inks, compositions carrying active ingredients such as UV absorbers, fragrances, biocides, antimicrobial agents, germicides, antioxidants, preservatives, disinfectants, enzymes, nutrients, minerals, and drugs (including pharmaceuticals which are active physiologically or pharmacologically, either topically or systemically). Compositions containing a thickener containing an ammonium salt are likely to be useful in certain types of hair care compositions.

The invention is illustrated by the following Example.

Example

A homopolymer of C18A was prepared using the following ingredients, C18A (100 part), mercaptoethanol (0.17 part ), t-amylperoxy 2-ethyl hexanoate (1.73 part, sold by Witco as Esperox 570P,75% active in liquid), and t-butyl peroxybenzoate (0.5 part, sold by Witco as Esperox 10). To a resin kettle equipped with overhead stirrer and condenser was added 20% of the monomers and chain transfer agents. The mixture in the resin kettle was heated to 110° C., and oxygen was removed from the system through nitrogen purge for about 30 min followed by addition of 20% of the starting initiator charge. After allowing sufficient time for any initial exotherm to abate, the remaining monomers, chain transfer agents and starting initiator were pumped into the reaction vessel over 60–90 min. The polymer mixture was allowed to continue reacting for 60 min followed by addition of the chase initiator and reaction for 60 min. The mixture was put under reduced pressure for 60 min to remove volatile residuals. The resulting polymer was a yellow to white solid having a weight average molecular weight of 950,000, a number average molecular weight of 230,000, and bulk viscosity of 2000 centipoise. The effectiveness of the polymer as a thickener for HPIB was measured as described above. The thickened oil product was opaque and had a viscosity of 5400 centipoise.

What is claimed is:

1. A thickened oil composition comprising
   (1) an oil, and
   (2) dispersed in the oil, a polymer which
      (a) has a crystalline melting point, $T_p$, and an onset of melting temperature, $T_o$, such that $T_p - T_o$ is less than $T_p^{0.7}$;
      (b) is soluble in the oil at temperatures above $T_p$,
      (c) has been dispersed in the oil by a process which comprises
         (i) dissolving the polymer in the oil at a temperature above $T_p$, and
         (ii) cooling the solution to crystallize the polymer in the oil,
      (d) is a side chain crystalline (SCC) polymer which is substantially free of functional groups, and which consists of
         (i) 50 to 100% by weight of units derived from at least one n-alkyl acrylate or methacrylate in which the n-alkyl group contains 12 to 50 carbon atoms, and
         (ii) 0 to 50% by weight of units derived from at least one alkyl acrylate or methacrylate in which the alkyl group is not an n-alkyl group containing 12 to 50 carbon atoms, and
      (e) is present in amount 3 to 10 % by weight;
   (ii) the composition being at a temperature below $T_p$.

2. A composition according to claim 1, wherein the SCC polymer consists essentially of units derived from an n-alkyl acrylate in which the n-alkyl group contains 14 to 22 carbon atoms.

3. A composition according to claim 1 which is at a temperature of 20 to 25° C. and wherein $T_p$ is more than 40° C.

4. A composition according to claim 1 which is substantially free of water.

5. A composition according to claim 1 wherein $T_p$ is 20–80° C.

6. A composition according to claim 1, wherein $T_p - T_o$ is less than 10° C.

7. A composition according to claim 1 which contains 3 to 7% by weight of the SCC polymer.

8. A thickened oil composition comprising
   (1) at least one oil selected from the group consisting of hydrogenated polyisobutylene; triglycerides; purcellin oil; isopropyl myristate; butyl myristate; cetyl myristate; isopropyl palmitate; butyl palmitate; ethyl-2-hexyl palmitate; isopropyl stearate; butyl stearate; octyl hexadecyl stearate; isocetyl stearate; decyl oleate; hexyl laurate; propylene glycol dicaprylate; diisopropyl adipate; animal oils; oleyl alcohol; linoleyl alcohol; linolenyl alcohol; isostearyl alcohol; octyl dodecanol; esters derived from lanolic acid; acetyl glycerides; octanoates of glycol; octanoates of glycerol; decanoates of glycol; decanoates of glycerol; and cetyl ricinoleate; and
   (2) dispersed in the oil, a polymer which
      (a) has a crystalline melting point, $T_p$, and an onset of melting temperature, $T_o$, such that $T_p - T_o$ is less than $T_p^{0.7}$,
      (b) is soluble in the oil at temperatures above $T_p$,
      (c) has been dispersed in the oil by a process which comprises (i) dissolving the polymer in the oil at a temperature above $T_p$, and (ii) cooling the solution to crystallize the polymer in the oil, and
      (d) is a side chain crystalline (SCC) polymer which is substantially free of functional groups, and which consists of
         (i) 50 to 100% by weight of units derived from at least one n-alkyl acrylate or methacrylate in which the n-alkyl group contains 12 to 50 carbon atoms, and
         0 to 50% by weight of units derived from at least one alkyl acrylate or methacrylate in which the alkyl group is not an n-alkyl group containing 12 to 50 carbon atoms;
   the composition being at a temperature below $T_p$.

9. A composition according to claim 8 wherein $T_p$ is above 40° C.

10. A composition according to claim 8 wherein $T_p$ is 20–80° C.

11. A composition according to claim 8 wherein $T_p - T_o$ is less than 10° C.

12. A composition according to claim 8 wherein the SCC polymer comprises a homopolymer of the n-alkyl acrylate in which the n-alkyl group contains 18 carbon atoms.

13. A composition according to claim 8 wherein the SCC polymer is a homopolymer of the n-alkyl acrylate in which the n-alkyl group contains 22 carbon atoms.

14. A composition according to claim 8 wherein the oil comprises a vegetable oil.

15. A composition according to claim 8 wherein the oil comprises at least one oil selected from the group consisting of sunflower seed oil, sesame seed oil, rape seed oil, sweet almond oil, calphyllum oil, palm oil, avocado oil, jojoba oil, olive oil, castor oil, and grain germ oils.

16. A composition according to claim 8 wherein the oil comprises at least one oil selected from the group consisting of perhydrosqualene, isopropyl lanolate and isocetyl lanolate.

17. A thickened oil composition which is a water-in-oil emulsion and which comprises
   (1) an oil, and
   (2) dispersed in the oil, a polymer which
      (a) has a crytalline melting point, $T_p - T_o$ is less than $T_p^{0.7}$,
      (b) is soluble in the oil at temperatures above $T_p$,
      (c) has been dispersed in the oil by a process which comprises
         (i) dissolving the polymer in the oil at a temperature above the $T_p$, and
         (ii) cooling the solution to crystallize the polymer in the oil,
      and
      (d) is a side chain crystalline (SCC) polymer which is substantially free of functional groups;
   the composition being at a temperature below $T_p$.

18. A thickened oil composition which is a water-in-oil emulsion and which comprises
(1) an oil, and
(2) dispersed in the oil, a side chain crystalline (SCC) polymer which
(a) has a crytalline melting point, $T_p$, of 20 to 80° C., an onset of melting temperature, $T_o$, such that $T_p-T_o$ is less than 10° C.,
(b) is soluble in the oil at temperatures above $T_p$,
(c) has been dispersed in the oil by a process which comprises
(i) dissolving the polymer in the oil at a temperature above the $T_p$, and
(ii) cooling the solution to crystallize the polymer in the oil,
(d) contains at least 80% by weight of repeating units containing a side chain comprising a linear polymethylene radical or a linear substantially perfluorinated polymethylene radical containing 6 to 50 carbon atoms, and
(e) is substantially free or functional groups;
the composition being at a temperature below $T_p$.

19. A composition according to claim 18, wherein $T_p$ is 20–80° C.

20. A composition according to claim 18, wherein the SCC polymer consists essentially of units derived from at least one n-alkyl acrylate or methacrylate in which the n-alkyl group contains 12 to 50 carbon atoms.

21. A composition according to claim 18 which contains 3 to 10% by weight of the SCC polymer.

22. A composition according to claim 18 which contains 3 to 7% by weight of the SCC polymer.

23. A thickened oil composition which is a lipstick, deodorant, nail varnish, sun cream, protective hand cream, night renewal cream, body milk, body lotion, light facial cream, protective day cream, or moisturizing emulsion; and which comprises
(1) an oil, and
(2) dispersed in the oil, a polymer which
(a) has a crytalline melting point, $T_p$, and an onset of melting temperature, $T_o$, such that $T_p-T_o$ is lesss than $T_p^{0.7}$,
(b) is soluble in the oil at temperatures above $T_p$,
(c) has been dispersed in the oil by a process which comprises
(i) dissolving the polymer in the oil at a temperature above the $T_p$, and
(ii) cooling the solution to crystallize the polymer in the oil, and
(d) is a side chain crystalline (SCC) homopolymer which is substantially free of functional groups;
the composition being at a temperature below $T_p$.

24. A thickened oil composition which is a lipstick, deodorant, nail varnish, sun cream, protective hand cream, night renewal cream, body milk, body lotion, light facial cream, protective day cream, or moisturizing emulsion, and which comprises
(1) an oil,
(2) dispersed in the oil, a polymer which
(a) has a crytalline melting point, $T_p$, and an onset of melting temperature, $T_o$, such that $T_p-T_o$ is lesss than $T_p^{0.7}$,
(b) is soluble in the oil at temperatures above $T_p$,
(c) has been dispersed in the oil by a process which comprises
(i) dissolving the polymer in the oil at a temperature above the $T_p$, and
(ii) cooling the solution to crystallize the polymer in the oil, and
(d) is a side chain crystalline (SCC) homopolymer which is substantially free of functional groups, and which consist of
(i) 50 to 100% by weight of units derived from at least one n-alkyl acrylate or methacrylate in which the n-alkyl group contains 12 to 50 carbon atoms, and
(ii) 0 to 50% by weight of units derived from at least one alkyl acrylate or methacrylate in which the alkyl group is not an n-alkyl group containing 12 to 50 carbon atoms;
the composition being at a temperature below $T_p$.

25. A composition according to claim 23, wherein the SCC polymer consists essentially of units derived from an n-alkyl acrylate or methacrylate in which the n-alkyl group contains 10 to 50 carbon atoms.

26. A composition according to claim 23 wherein the SCC polymer is present in amount 0.1 to 12% by weight, based on the weight of the oil.

27. A composition according to claim 23 which contains 3 to 10% by weight of the SCC polymer.

28. A composition according to claim 23 which contains 3 to 7% by weight of the SCC polymer.

29. A composition according to claim 23 wherein $T_p$ is more than 40° C.

30. A composition according to claim 23 wherein $T_p$ is 20 to 80° C.

31. A composition according to claim 23 which is at a temperature of 20 to 25° C. and wherein $T_p$ is 40–50° C.

32. A composition according to claim 23, wherein $T_p-T_o$ is less than 10° C.

33. A composition according to claim 23 which is substantially free of water.

34. A thickened oil composition which is a pretanning lotion, sunscreen lotion, sun tan lotion, , after-sun lotion, makeup remover, hair-treating oil, hairdressing preparation, shampoo, foam bath, bath oil, skin cleanser, skin foundation, perfumed gel, mascara or eye makeup, and which comprises
(1) an oil, and
(2) dispersed in the oil, a polymer which
(a) has a crystalline melting point, $T_p$, and an onset of melting temperature, $T_o$, such that $T_p-T_o$ is less than $T_p^{0.7}$,
(b) is soluble in the oil at temperatures above $T_p$,
(c) has been dispersed in the oil by a process which comprises
(i) dissolving the polymer in the oil at a temperature above $T_p$, and
(ii) cooling the solution to crystallize the polymer in the oil;
and
(d) is a side chain crystalline (SCC) polymer which is substantially free of functional groups;
the composition being at a temperature which is below $T_p$.

35. A composition according to claim 34 which is substantially free of water.

36. A composition according to claim 34 wherein the SCC polymer is present in amount 0.1 to 12% by weight, based on the weight of oil.

37. A composition according to claim 34 which contains 3 to 10% by weight of the SCC polymer.

38. A composition according to claim 34 which contains 3 to 7% by weight of the SCC polymer.

39. A composition according to claim 34 wherein $T_p$ is more than 40° C.

40. A composition according to claim 34 wherein $T_p$ is 20 to 80° C.

41. A composition according to claim 34 which is at a temperature of 20 to 25° C. and $T_p$ is 40–50° C.

42. A composition according to claim 35, wherein $T_p$-$T_o$ is less than 10° C.

43. A composition which comprises
  (1) an oil,
  (2) dispersed in the oil, a polymer which
    (a) has a crystalline melting point, $T_p$, and an onset of melting temperature, $T_o$, such that $T_p$-$T_o$ is less than $T_p^{0.7}$,
    (b) is soluble in the oil at temperatures above $T_p$,
    (c) has been dispersed in the oil by a process which comprises
      (i) dissolving the polymer in the oil at a temperature above $T_p$, and
      (ii) cooling the solution to crystallize the polymer in the oil;
    and
    (d) is a side chain crystalline (SCC) polymer which is substantially free of functional groups; and
  (3) at least one additive selected from the group consisting of sunscreen agents, deodorants, pharmaceuticals and antiseptic agents;
the composition being at a temperature which is below $T_p$.

44. A composition according to claim 43 which is substantially free of water.

45. A composition according to claim 43 wherein the SCC polymer is present in amount 0.1 to 12% by weight, based on the weight of the oil.

46. A composition according to according to claim 43 which contains 3 to 10% by weight of the SCC polymer.

47. A composition according to claim 43 which contains 3 to 7% by weight of the SCC polymer.

48. A composition according to claim 43 wherein $T_p$ is more than 40° C.

49. A composition according to claim 43 wherein $T_p$ is 20 to 80° C.

50. A composition according to claim 43 which is at a temperature of 20 to 25° C. and wherein $T_p$ is 40–50° C.

51. A composition according to claim 43 wherein $T_p$-$T_o$ is less than 10° C.

52. A composition according to claim 43 which is substantially free of water.

53. A thickened oil composition which comprises
  (1) a silicone oil,
  (2) dispersed in the oil, a polymer which
    (a) has a crystalline melting point, $T_p$, and an onset of melting temperature, $T_o$, such that $T_p$-$T_o$ is less than $T_p^{0.7}$,
    (b) is soluble in the oil at temperatures above $T_p$,
    (c) has been dispersed in the oil by a process which comprises
      (i) dissolving the polymer in the oil at a temperature above $T_p$, and
      (ii) cooling the solution to crystallize the polymer in the oil; and
    (d) is a side chain crystalline (SCC) polymer which is substantially free of functional groups;
the composition being at a temperature which is below $T_p$.

* * * * *